US006911308B2

(12) United States Patent
Shuber (10) Patent No.: US 6,911,308 B2
(45) Date of Patent: Jun. 28, 2005

(54) METHODS FOR DETECTING, GRADING OR MONITORING AN H. PYLORI INFECTION

(75) Inventor: Anthony P. Shuber, Milford, MA (US)

(73) Assignee: Exact Sciences Corporation, Marlborough, MA (US)

(*) Notice: Subject to any disclaimer, the term of this patent is extended or adjusted under 35 U.S.C. 154(b) by 68 days.

(21) Appl. No.: 09/755,004

(22) Filed: Jan. 5, 2001

(65) Prior Publication Data

US 2002/0110810 A1 Aug. 15, 2002

(51) Int. Cl.[7] ............................ C12Q 1/68; C12P 19/34; C07H 21/02
(52) U.S. Cl. ......................... 435/6; 435/91.2; 536/23.1
(58) Field of Search .................... 435/6, 91.2; 536/23.1, 536/24.33, 22.1

(56) References Cited

U.S. PATENT DOCUMENTS

| | | | |
|---|---|---|---|
| 5,401,631 A | 3/1995 | Lane et al. ..................... | 435/6 |
| 5,670,325 A | 9/1997 | Lapidus et al. ................ | 435/6 |
| 5,705,332 A | 1/1998 | Roll ............................... | 435/6 |
| 5,741,650 A | 4/1998 | Lapidus et al. ................ | 435/6 |
| 5,795,717 A | 8/1998 | Nakayama et al. ............ | 435/6 |
| 5,830,665 A | 11/1998 | Shuber et al. ................. | 435/6 |
| 5,888,778 A | 3/1999 | Shuber ...................... | 435/91.1 |
| 5,928,870 A | 7/1999 | Lapidus et al. ................ | 435/6 |
| 5,952,178 A | 9/1999 | Lapidus et al. ................ | 435/6 |
| 5,958,686 A | 9/1999 | Houng .......................... | 435/6 |
| 6,020,137 A | 2/2000 | Lapidus et al. ................ | 435/6 |
| 6,100,029 A | 8/2000 | Lapidus et al. ................ | 435/6 |
| 6,143,529 A * | 11/2000 | Lapidus et al. ............ | 435/91.2 |
| 6,146,828 A | 11/2000 | Lapidus et al. ................ | 435/6 |
| 6,203,993 B1 | 3/2001 | Shuber et al. ................. | 435/6 |
| 6,214,187 B1 | 4/2001 | Hammond et al. ......... | 204/450 |
| 6,214,558 B1 | 4/2001 | Shuber et al. ................. | 435/6 |
| 6,238,927 B1 | 5/2001 | Abrams et al. ............... | 436/94 |
| 6,251,660 B1 | 6/2001 | Muir et al. ............... | 435/287.2 |
| 6,268,136 B1 | 7/2001 | Shuber et al. ................. | 435/6 |
| 6,280,947 B1 | 8/2001 | Shuber et al. ................. | 435/6 |
| 6,300,077 B1 | 10/2001 | Shuber et al. ................. | 435/6 |
| 6,303,304 B1 | 10/2001 | Shuber et al. ................. | 435/6 |
| 6,351,857 B2 | 3/2002 | Slaon, III et al. ............. | 4/315 |
| 2001/0018180 A1 | 8/2001 | Shuber et al. ................. | 435/6 |
| 2002/0004201 A1 | 1/2002 | Lapidus et al. ................ | 435/6 |
| 2002/0025525 A1 | 2/2002 | Shuber .......................... | 435/6 |
| 2002/0045183 A1 | 4/2002 | Shuber et al. ................. | 435/6 |
| 2002/0048752 A1 | 4/2002 | Lapidus et al. ................ | 435/6 |
| 2002/0064787 A1 | 5/2002 | Shuber et al. ................. | 435/6 |
| 2002/0119469 A1 | 8/2002 | Shuber et al. ................. | 435/6 |
| 2002/0119472 A1 | 8/2002 | Lapidus et al. ................ | 435/6 |
| 2002/0123060 A1 | 9/2002 | Boles et al. ................... | 435/6 |
| 2002/0132251 A1 | 9/2002 | Shuber .......................... | 435/6 |
| 2002/0164631 A1 | 11/2002 | Shuber et al. ................. | 435/6 |
| 2002/0172955 A1 | 11/2002 | Adams et al. ................. | 435/6 |
| 2003/0044780 A1 | 3/2003 | Lapidus et al. ................ | 435/6 |

FOREIGN PATENT DOCUMENTS

| | | | |
|---|---|---|---|
| AU | 711754 | 7/1997 | ............ C12Q/1/68 |
| AU | 704696 | 8/1997 | ......... G01N/33/574 |
| AU | 730491 | 11/1998 | ............ C12Q/1/68 |
| AU | 720489 | 9/1999 | ............ C12Q/1/68 |
| CA | 2211702 | 5/1999 | ............ C12Q/1/68 |
| WO | WO 91/09049 * | 6/1991 | |
| WO | WO 00/29618 * | 5/2000 | |
| WO | WO 00/50640 | 8/2000 | ............ C12Q/1/68 |
| WO | WO 00/70096 | 11/2000 | ............ C12Q/1/68 |
| WO | WO 01/18252 | 3/2001 | ............ C12Q/1/68 |
| WO | WO 01/42502 | 6/2001 | ............ C12Q/1/68 |
| WO | WO 01/42503 | 6/2001 | ............ C12Q/1/68 |
| WO | WO 01/42781 | 6/2001 | .......... G01N/33/48 |
| WO | WO 01/53817 | 7/2001 | .......... G01N/27/00 |
| WO | WO 01/64950 | 9/2001 | ............ C12Q/1/68 |
| WO | WO 02/059379 A2 | 8/2002 | ............ C12Q/1/68 |

OTHER PUBLICATIONS

Gramley W A et al. Detection of *Helicobacter pylori* DNA in Fecal Samples. J. Clin. Microbiol., vol. 37 (7), pp. 2236–2240, 1999.*

Li et al. A newly developed PCR assay of *H. pylori* in gastric biopsy, saliva, and feces. Digestive Diseases and Sciences, vol. 41(11), pp. 2142–2149, 1996.*

Chong et al. Evaluation of 16S rRNA gene PCR with primers Hp1 and Hp2 for detection of *Helicobacter pylori*. J Clin Microbiol., vol. 34(11): 2728–2730, 1996.*

Li C et al. High prevalence of *Helicobacter pylori* in saliva demonstrated by a novel PCR assay. J Clin Pathol., vol. 48: 662–666, 1995.*

Anderson, J., "*H pylori* infection: Review of the guideline for diagnosis and treatment," *Geriatrics* 55: 44–49 (Jun. 2000).

Caselli et al., "Diagnosis of *Helicobacter pylori* infection by $H_pSA$ test," *Lancet,* 354(*9185*): 1209–1210.

Correa et al., "Chemoprevention of Gastric Dysplasia: Randomized Trial of Antioxidant Supplements and Anti–*Helicobacter pylori* Therapy," *J. National Cancer Institute,* 92(*23*): 1881–1888 (Dec. 2000).

Costa et al., "Post–treatment diagnostic accuracy of a new enzyme immunoassay to detect *Helicobacter pylori* in stools." *Aliment. Pharmacol. Ther.,* 15: 395–401 (2001).

Doig et al., "*Helicobacter pylori* Physiology Predicted from Genomic Comparison of Two Strains," *Microbiol. and Molecular Biol. Reviews,* 63(*3*): 675–707 (Sep. 1999).

(Continued)

*Primary Examiner*—Jeffrey Fredman
*Assistant Examiner*—Prabha Chunduru
(74) *Attorney, Agent, or Firm*—Mintz, Levin, Cohn, Ferris, Glovsky and Popeo, P.C.; Ivor R. Elrifi, Esq.; Naomi S. Biswas, Esq.

(57) ABSTRACT

The present invention provides methods for determining the status of an *H. pylori* infection by detecting a high-integrity *H. pylori* nucleic acid in a patient sample.

14 Claims, 5 Drawing Sheets

OTHER PUBLICATIONS

Duggan, A.E., "Testing for *Helicobacter pylori* infection: validation and diagnostic yield of a near patient test in primary care," *British Medical Journal, 319*: 1236–1239 (Nov. 1999).

Dunn et al., "*Helicobacter pylori*," *Clin. Microbiol. Reviews, 10(4)*: 720–741 Oct. 1997).

Forné et al., "Accuracy of an Enzyme Immunoassay for the Detection of *Helicobacter pylori* in Stool Specimens in the Diagnosis of Infection and Posttreatment Check–Up," *Am. J. Gastroenter., 95(9)*: 2200–2205 (Sep. 2000).

Fox et al., "*Helicobacter pylori*—Not a Good Bug After All," *N. Engl. J. Med., 345(11)*: 829–832 (Sep. 2001).

Gramley et al., "Detection of *Helicobacter pylori* DNA in Fecal Samples from Infected Individuals," *J. Clin. Microbiol., 37(7)*: 2236–2240 (Jul. 1999).

"*H. pylori* Drug Resistance a Growing Problem in Germany," *Reuters Medical News*, downloaded from www.medscape.com/viewarticle/429645_print on Mar. 13, 2002.

"*H. pylori* Eradication May Improve Platelet Count in Thrombocytopenia," *Reuters Medical News*, downloaded from http://gastroenterology.medscape.com/reu.../prof/2001/02/02.09/20010208clin005.htp on Feb. 12, 2001.

"*Helicobacter pylori* and Gastric Lymphoma: A Dangerous Connection," *Medscape Hematology—Oncology, 4(2)*: (2001), downloaded from http://gastroenterology.medscape.com/Medscape/oncology/journal/2001/v04.n02/ca–mo042... on Apr. 29, 2001.

Herbrink et al., "Serological Methods for Diagnosis of *Helicobacter pylori* Infection and Monitoring of Eradication Therapy," *Eur. J. Clin. Microbiol. Infect. Dis., 19*: 164–173 (2000).

Ishihara et al., "Diagnostic accuracy of a new non–invasive enzyme immunoassay for detecting *Helicobacter pylori* in stools after eradication therapy," *Aliment. Pharmacol. Ther., 14*: 611–614 (2000).

Kerr et al., "An association between sudden infant death syndrome (SIDS) and *Helicobacter pylori* infection," *Arch. Dis. Child., 83*: 429–434 (2000).

Marais et al., "Metabolism and Genetics of *Helicobacter pylori*: the Genome Era," *Microbiol. and Molec. Biol. Reviews. 63(3)*: 642–674 (Sep. 1999).

Moayyedi et al., "The effectiveness of omeprazole, clarithromycin and tinidazole in eradicating *Helicobacter pylori* in a community screen and treat programme," *Aliment. Pharmacol. Ther., 14*: 719–728 (2000).

Monteiro et al., "Detection of *Helicobacter pylori* DNA in human feces by PCR: DNA stability and removal of inhibitors," *J. Microbiol. Meth., 45*: 89–94 (2001).

Monteiro et al., "Magnetic Immuno–PCR Assay with Inhibitor Removal for Direct Detection of *Helicobacter pylori* in Human Feces," *J. Clin. Microbiol., 39(10)*: 3778–3780 (Oct. 2001).

Ni et al., "Accurate diagnosis of *Helicobacter pylori* infection by stool antigen test and 6 other currently available tests in children," *J. Pediatrics, 136(6)*: 823–827 (Jun. 2000).

Nilsson et al., "*Helicobacter* Species Identified in Liver From Patients With Cholangiocarcinoma and Hepatocellular Carcinoma," *Gastroenterology, 120(1)*: 323–326 (Jan. 2001).

Peña et al., "Molecular Resistance Testing of *Helicobacter pylori* in Gastric Biopsies," *Arch. Pathol. Lab. Med., 125*: 493–497 (Apr. 2001).

Peterson et al., "*Helicobacter pylori*, " in Slesinger et al., *Gastrointestinal and Liver Disease: Pathophysiology/Diagnosis/Management*, Philadelphia: W.B. Saunders, 1998: 604–615.

Shepherd et al., "Comparison of an enzyme immunoassay for the detection of *Helicobacter pylori* antigens in the faeces with the urea breath test," *Arch. Dis. Child., 83*: 268–270 (2000).

Shuber et al., "Accurate Non–invasive Detection of *H. pylori* DNA before and After Treatment," oral presentation, (May 2001).

Uemura et al., "*Helicobacter pylori* infection and the Development of Gastric Cancer," *New England J. of Med., 345(11)*: 784–789 (Sep. 2001).

Vaira, D., "Diagnosis of *Helicobacter pylori* infection with a new non–invasive antigen–based assay," *Lancet, 354*: 30–33 (Jul. 1999).

Yamamoto et al., "A New Rapid Test for Detecting Anti–*Helicobacter pylori* Antibody Excreted into Urine," *Helicobacter, 5(3)*: 160–164 (2000).

Zipser et al., "Is Repeat Testing Needed for *Helicobacter pylori*?," *J. Am. Board of Fam. Prac., 13(6)*: 449–450 (2000).

Bélanger et al., "Rapid Detection of *Clostridium difficile* in Feces by Real–Time PCR," *J. Clin. Microbiol., 41(2)*: 730–734 (Feb. 2003).

Bickley et al., "Evaluation of the polymerase chain reaction for detecting the urease C gene of *Helicobacter pylori* in gastric biopsy samples and dental plaque," *J. Med. Microbiol., 39(5)*: 338–344 (1993).

Bravos et al., "Accurate Diagnosis of *Helicobacter pylori*," *Gastroenterology Clinics of North America, 29(4)*: 925–929 (Dec. 2000).

Johnston et al., "Evaluation of Three Commercial Assays for Detection of *Giardia* and *Cryptosporidium* Organisms in Fecal Specimens," *J. Clin. Microbiol., 41(2)*: 623–626 (Feb. 2003).

Kawamata et al., "Nested–Polymerase Chain Reaction for the Detection of *Helicobacter pylori* Infection with Novel Primers Designed by Sequence Analysis of Urease A Gene in Clinically Isolated Bacterial Strains," *Biochem. And Biophys. Research Comm., 219(1)*: 266–272 (Feb. 1996).

Mapstone et al., "Identification of *Helicobacter pylori* DNA in the mouths and stomachs of patients with gastritis using PCR," *J. Clin. Pathol., 46(6)*: 540–543 (Jun. 1993).

Monteiro, et al., "Complex Polysaccharides as PCR Inhibitors in Feces: *Helicobacter pylori* Model," *J. Clin. Microbiol., 35(4)*: 995–998 (Apr. 1997).

Nagashima et al., "Application of New Primer–Enzyme Combinations to Terminal Restriction Fragment Length Polymorphism Profiling of Bacterial Populations in Human Feces," *Applied and Environ. Microbiol., 69(2)*: 1251–1262 (Feb. 2003).

Osaki, et al., "Detection of *Helicobacter pylori* in Fecal Samples of Gnotobiotic Mice Infected with *H. pylori* by an Immunomagnetic–Bead Separation Technique," *J. Clin. Microbiol., 36(1)*: 321–323 (Jan. 1998).

Shuber et al., "Accurate, Noninvasive Detection of *Helicobacter pylori* DNA from Stool Samples: Potential Usefulness for Monitoring Treatment," *J. Clin. Microbiol., 40(1)*: 262–264 (Jan. 2002).

Song et al., "*Helicobacter pylori* in Dental Plaque: A Comparison of Different PCR Primer Sets," *Digestive Dis. and Sci., 44(3)*: 479–484 (Mar. 1999).

Uribe et al., "Sensitive Detection of *Helicobacter pylori* in Gastric Aspirates by Polymerase Chain Reaction," *The Journal of the Japanese Association for Infectious Diseases*, 72(2): 114–122 (Feb. 1998).

Watanabe, et al., "Detection of *Helicobacter pylori* Gene by Means of Immunomagnetic Separation–Based Polymerase Chain Reaction in Feces," *Scandinavian Journal of Gastroenterology*, 33(11): 1140–1143 (1998).

Weiss et al., "Comparison of PCR and Other Diagnostic Techniques for Detection of *Helicobacter pylori* Infection in Dyspeptic Patients," *J. Clin. Microbiol.*, 32(7): 1663–1668 (Jul. 1994).

Westblom, et al., "Diagnosis of *Helicobacter pylori* Infection by means of a Polymerase Chain Reaction Assay for Gastric Juice Aspirates," *Clin. Infectious Dis.*, 16(3): 367–371 (Mar. 1993).

Yoshida et al., "Use of a Gastric Juice–Based PCR Assay To Detect *Helicobacter pylori* Infection in Culture–Negative Patients," *J. Clin. Microbiol.*, 36(1): 317–320 (Jan. 1998).

Fermér et al., "Development and Use of a Simple Polymerase Chain Reaction Assay to Screen for *Helicobacter* spp. and *H. hepaticus* in Intestinal and Fecal Samples from Laboratory Mice," *Comparative Medicine*, 52(16):518–522 (Dec. 2002).

Riley et al., "Identification of Murine Helicobacters by PCR and Restriction Enzyme Analyses," *J. Clinical Microbiology*, 34(4):942–946 (Apr. 1996).

Chong et al., "Evaluation of 16S rRNA Gene PCR with Primers Hp1 and Hp2 for Detection of *Helicobacter pylori*", *Journal of Clinical Microbiology*, 34(11): 2728–2730 (Nov. 1996).

Enroth et al., "Immunomagnetic Separation and PCR for Detection of *Helicobacter pylori* in Water and Stool Specimens", *Journal of Clinical Microbiology*, 33(8): 2162–2165 (Aug. 1995).

Franks et al., "Variations of Bacterial Populations in Human Feces Measured by Fluorescent In Situ Hybridization with Group–Specific 16S rRNA–Targeted Oligonucleotide Probes", *Applied and Environmental Microbiology*, 64(9): 3336–3345 (Sep. 1998).

Gramley et al., "Detection of *Helicobacter pylori* DNA in Fecal Samples from Infected Individuals", *Journal of Clinical Microbiology*, 37(7): 2236–2240 (Jul. 1999).

Harmsen et al., "Analysis of Intestinal Flora Development in Breast–Fed and Formula Fed Infants by Using Molecular Identification and Detection Method", *Journal of Pediatric Gastroenterology and Nutrition*, 30(1): 61–67 (Jan. 2000).

Harmsen et al., "Comparison of viable cell counts and fluorescence in situ hybridization using specific rRNA–based probes for the quantification of human fecal bacteria", *FEMS Microbiology Letters*, 183: 125–129 (1999).

Ishihara et al., "Diagnostic accuracy of a new non–invasive enzyme immunoassay for detecting *Helicobacter pylori* in stools after eradication therapy", *Altment Pharmacol Ther.* 14: 611–614 (2000).

Li et al., "A Newly Developed PCR Assay of *H. pylori* in Gastric Biopsy, Saliva and Feces Evidence of High Prevalence of *H. pylori* in Saliva Supports Oral Transmission", *Digestive Diseases and Sciences*, 41(11): 2142–2149 (Nov. 1996).

Makristathis et al., "Detection of *Helicobacter pylori* in Stool Specimens by PCR and Antigen Enzyme Immunoassay", *Journal of Clinical Microbiology*, 36(9): 2772–2774 (Sep. 1998).

Namavar et al., "Presence of *Helicobacter pylori* in the Oral Cavity, Oesophagus, Stomach and Faeces of Patients with Gastritis", *European Journal of Clinical Microbiology &Infectious Diseases*, 14(3): 234–237 (Mar. 1995).

Parsonnet et al., "Fecal and Oral Shedding of *Helicobacter pylori* From Healthy Infected Adults", *The Journal of the American Medical Association*, 282(23): 2240–2245 (Dec. 15, 1999).

Westblom, "Molecular Diagnosis of *Helicobacter pylori*", *Immunological Investigations*, 26(1–2): 163–174 (1997).

Makristathis et al., "Two Enzyme Immunoassays and PCR for Detection of *Helicobacter pylori* in Stool Specimens from Pediatric Patients before and after Eradication Therapy," *J. Clin. Microbiol.*, 38(10): 3710–3714 (Oct. 2000).

Giacona et al., "Cell–Free DNA in Human Blood Plasma: Length Measurements in Patients with Pancreatic Cancer and Healthy Controls," *Pancreas*, 17(1): 89–97 (1998).

Husson et al., "Importance in Diagnosis of Gastritis of Detection by PCR of the cagA Gene *Helicobacter pylori* Strains Isolated from Children," *J. Clin. Microbiol.*, 33(12): 3300–3303 (Dec. 1995).

Lu et al., "Comparison of Five PCR Methods for Detection of *Helicobacter pylori* DNA in Gastric Tissues," *J. Clin. Microbiol.*, 37(3): 772–774 (Mar. 1999).

Riggio et al., "Detection of *Helicobacter pylori* DNA in recurrent aphthous stomatitis tissue by PCR," *J. Oral Pathol. Med.*, 29: 507–513 (2000).

Wagner et al., "Regulation of Gastric Epithelial Cell Growth by *Helicobacter pylori*: Evidence for a Major Role of Apoptosis," *Gastroenterology*, 113: 1836–1847 (Dec. 1997).

Patent Cooperation Treaty, International Search Report, International Application No. PCT/US 02/00267, mailed on Jul. 2, 2003, 5 pages.

* cited by examiner

METHODS FOR DETECTING, GRADING OR MONITORING AN *H. PYLORI* INFECTION

BACKGROUND OF THE INVENTION

*Helicobacter pylori* (*H. pylori*) has been implicated in a variety of gastrointestinal diseases such as gastritis, gastric and duodenal ulcers, and gastric malignancies. *H. pylori* infections are generally persistent, causing chronic gastrointestinal disease. Treating an *H. pylori* infection can dramatically improve the gastrointestinal health of the patient. Ulcers, for example, become much less likely to recur following successful treatment of an infection. Unfortunately, conventional treatments for *H. pylori* infections are not always successful. Accordingly, there is a need for assays to confirm that the infection has been cured.

Assays for *H. pylori* infections have been developed. Many assays are invasive, requiring endoscopy followed by culture, histology, or other procedures. More recently, less invasive methods have been developed. One method tests serum for antibodies to *H. pylori* (see, e.g., Li et al., Dig. Dis. Sciences, 41: 2142–2149 (1996)); another tests for $CO_2$ produced by *H. pylori* urease activity (see, e.g., Westblom, Immunol. Invest., 26:163–174 (1997)). Immunoassay and PCR methods to detect *H. pylori* have also been developed. See, e.g., Gramley et al., J. Clin. Microbiol., 37:2236–2240 (1999); Ishihara et al., Aliment. Pharmacol. Ther., 14: 611–614 (2000); Namavar et al., Eur. J. Clin. Microbiol. Infect. Dis., 14:234–237 (1995); Parsonnet et al., JAMA, 282: 2240–2245 (1999). PCR-based methods may have advantages to some of the other methods (low cost, high throughput, etc.). Unfortunately, PCR-based methods known in the art may lack the specificity to distinguish, for example, a successfully treated patient from a patient with a continuing *H. pylori* infection. See, e.g., Makristathis et al., J. Clin. Microbiol., 36: 2772–2774 (1998). There exists a continuing need for non-invasive assays to test for and to monitor *H. pylori* infection and course of treatment.

SUMMARY OF THE INVENTION

Methods of the invention provide invasive, minimally-invasive or non-invasive methods for *H. pylori* screening and monitoring. Methods of the invention comprise detecting the presence of high-integrity *H. pylori* nucleic acid in a sample obtained from a patient who preferably has at least one symptom (e.g. stomach pain) indicative of a gastrointestinal disorder. The presence of high-integrity *H. pylori* nucleic acid in a patient sample means that the patient from whom the sample was obtained has an active *H. pylori* infection. The amount of high-integrity *H. pylori* nucleic acid is an indicator of the severity of infection or the extent to which a treatment has reduced infection. The presence of an *H. pylori* infection in a patient can be determined and distinguished from a past, cured infection. Indeed, the sensitivity and specificity of methods of the invention make it possible to estimate the current degree of severity of an infection and to monitor the progress of an infection or of a course of treatment.

The invention relies on methods for detecting high-integrity nucleic acid associated with *H. pylori* infection. For purposes of the invention, a high-integrity nucleic acid is one having about 175 base pairs or more. According to the invention, the presence and/or amount of such high-integrity nucleic acid is indicative of the presence and severity of infection.

In a preferred embodiment, the invention provides methods for detecting an ongoing *H. pylori* infection in a patient based on the presence of high-integrity *H. pylori* nucleic acid present in a biological sample obtained from a patient. According to the methods of the invention, high-integrity *H. pylori* nucleic acid is amplified in a patient sample. If the *H. pylori* nucleic acid is present in the patient sample, the patient has an ongoing *H. pylori* infection. In a preferred embodiment, the high-integrity nucleic acid assayed is a substantially intact *H. pylori* nucleic acid. The patient sample may include any tissue or fluid containing detectable, intact *H. pylori* nucleic acid (e.g. DNA). Preferred samples include stool, sputum, pancreatic fluid, bile, lymph, blood, urine, saliva, gastric juice, and vomitus, with stool or saliva being particularly preferred in some embodiments. Other samples, such as surgically excised solid tissues, may also be used in some embodiments of the invention.

The invention also provides methods for determining the status of an *H. pylori* infection by determining the integrity of an *H. pylori* nucleic acid present in a patient sample. A patent can be identified as having an *H. pylori* infection if the integrity of an *H. pylori* nucleic acid present in a sample from the patient exceeds a predetermined threshold. Such a threshold could be defined, for example, by a minimum number or percentage of *H. pylori* nucleic acids having a minimum length or having a particular intact fragment. The threshold may correspond to a detection threshold of an assay, or to a threshold above the detection threshold.

The invention further provides methods for grading an *H. pylori* infection in a patient. According to the methods of the invention, the amount of an intact *H. pylori* nucleic acid present in a patient sample is determined. This amount is compared to at least two standards indicative of different grades of infection (at least one of which may optionally indicate an absence of infection). By identifying a standard amount that corresponds to the sample amount (e.g. by identifying the standard amount closest to the sample amount, or by identifying the largest standard amount that is less than or equal to the sample amount, etc.), a patient can be classified as having a grade of *H. pylori* infection indicated by the corresponding standard.

According to a preferred embodiment of the invention, the progression of an *H. pylori* infection in a patient can be monitored. To monitor the progression of the infection, samples are taken from the patient over a period of time, and an amount of an intact *H. pylori* nucleic acid present in each sample is determined. By comparing the amounts of intact *H. pylori* nucleic acid in subsequent samples, the infection can be classified as diminishing (if the amount of intact nucleic acid is decreasing over time), stable (if the amount of intact nucleic acid is stable over time), or worsening (if the amount of intact nucleic acid is increasing over time). In a preferred embodiment, the period of time between samples is no more than thirty days. In more preferred embodiments, the time between samples is no more than seven days, or no more than four days.

The invention also provides methods for evaluating a course of treatment for an *H. pylori* infection. A sample can be obtained from a patient during a course of treatment for an *H. pylori* infection, or shortly thereafter (e.g. within thirty days). An intact *H. pylori* nucleic acid in the patient sample is amplified, and the patient is identified as having an ongoing *H. pylori* infection if the intact *H. pylori* nucleic acid is present in the sample. Similarly, the invention provides methods for evaluating a proposed treatment regimen by subjecting infected individuals to either a proposed treatment regimen or an established (control) treatment regimen, and following the patients during or shortly after their treatment regimens by amplifying an intact *H. pylori* nucleic acid in a sample from the patient. Reduced levels or frequencies of intact *H. pylori* nucleic acid in samples from individuals following the proposed treatment regimen correlate with improved efficacy of the treatment regimen. Alternatively, or in addition, an improved treatment regimen may be associated with an earlier reduction of intact *H. pylori* nucleic acid (e.g. by day 6 of a treatment regimen, or by day 4 of a treatment regimen), compared to a control regimen.

Methods of the invention are also useful for diagnosing a gastric disease in a patient. By detecting high-integrity *H. pylori* nucleic acid in a sample from a patient, the patient can be identified as having a gastric disease associated with an *H. pylori* infection.

The invention is also useful to determine the status of an *H. pylori* infection in a patient by amplifying, from a patient sample, a number of *H. pylori* nucleic acids (e.g. DNAs). In one embodiment, at least three *H. pylori* nucleic acids are amplified. Preferably, each nucleic acid has a different size; more preferably, the sizes span a range of at least 500 nucleotides. In a preferred embodiment, one *H. pylori* nucleic acid at least 200 nucleotides long, a second *H. pylori* nucleic acid at least 400 nucleotides long, and a third *H. pylori* nucleic acid at least 600 nucleotides long are amplified. Each nucleic acid is amplified, and the patient is identified as having an *H. pylori* infection if at least three amplified *H. pylori* nucleic acids are detected. Preferred samples include stool, sputum, pancreatic fluid, bile, lymph, blood, urine, saliva, gastric juice, and vomitus, with stool and saliva being particularly preferred in some embodiments. Other samples, such as surgically excised solid tissues, may also be used in some embodiments of the invention.

According to a preferred method of the invention, both an *H. pylori* nucleic acid and a non-*H. pylori* nucleic acid are detected. In one preferred embodiment, the non-*H. pylori* nucleic acid serves as a control for the integrity of the patient sample and the quality of the sample preparation technique. In this preferred embodiment, the non-*H. pylori* nucleic acid is preferably uniformly present both in patient samples from patients with an *H. pylori* infection and in patient samples from patients without an *H. pylori* infection. Accordingly, in one preferred embodiment, the non-*H. pylori* nucleic acid is a patient nucleic acid. In another preferred embodiment, the non-*H. pylori* nucleic acid is a nucleic acid from a foreign organism routinely present in patient samples. For example, in one preferred embodiment in which the patient sample is a stool sample, the non-*H. pylori* nucleic acid is an *Escherichia coli* nucleic acid.

In preferred methods of the invention including detection of both an *H. pylori* nucleic acid and a non-*H. pylori* nucleic acid, the non-*H. pylori* nucleic acid is preferably subjected to treatments identical with or analagous to the treatments of the *H. pylori* nucleic acid. For example, in a preferred embodiment of the method in which the amount of an *H. pylori* nucleic acid is determined, the amount of a non-*H. pylori* nucleic acid is preferably also determined. By comparing the amount of the *H. pylori* and the non-*H. pylori* nucleic acid, an amount of *H. pylori* nucleic acid relative to an amount of a control, non-*H. pylori* nucleic acid can be determined, providing more sensitive diagnostic information. A relative amount of a nucleic acid could be expressed as a ratio, a difference, or by other means expressing the relation between the *H. pylori* and non-*H. pylori* nucleic acids. The absolute amounts of the nucleic acids need not necessarily be determined, other information indicative of the relative abundance of the nucleic acids may be sufficient to determine the relative amounts. Similarly, in a preferred embodiment in which the integrity of an *H. pylori* nucleic acid is determined, the integrity of a non-*H. pylori* nucleic acid is preferably also determined to permit a comparison of the integrities of the *H. pylori* and non-*H. pylori* nucleic acids.

The invention also provides methods for detecting an *H. pylori* infection in a patient by determining the integrity of the patient's own DNA in a sample comprising shed cells or cellular material from the patient. According to the invention, certain tissue or body fluid samples, especially those described below, contain debris from cells that have been shed from surrounding organs or tissue. In healthy patients, such debris is the result of apoptosis as part of the normal cell cycle. Apoptosis reduces nucleic acid integrity, so that only small-fragment nucleic acids exist in exfoliated cellular debris in healthy individuals. In contrast, an infection caused by an organism such as *H. pylori* may result in the shedding of cells, such as epithelial cells or white blood cells, that have not undergone apoptosis. These cells may include living cells, such as blood cells released into the gastrointestinal tract by an ulcer, or cells that have died without undergoing apoptosis, through the action of the pathogen or as a result of an immune response, for example.

Accordingly, the methods of the invention permit the diagnosis of a patient as having an *H. pylori* infection if the integrity of the patient's nucleic acids in a sample including shed cells or cellular debris exceeds a predetermined threshold. As discussed above, the threshold could be defined, for example, by a minimum number or percentage of high-integrity patient nucleic acids, and the threshold may correspond to a detection threshold of an assay, or to a threshold above the detection threshold.

In a preferred embodiment of the methods, the integrity of the nucleic acids is determined by detecting a plurality of nucleic acids over a range of sizes (e.g. from 175–800 bp, from 400–1600 bp, or from 200–2300 bp). The presence of larger fragments is indicative of the integrity of the nucleic acid. For example, in a preferred embodiment using PCR detection of a nucleic acid in a patient sample, a 200 bp fragment is detected if a nucleic acid is, for example, 250 bases, 800 bases, or 3500 bases in length: the size of the detected PCR product is indicative of a minimum length of a nucleic acid present in the patient sample. Similarly, a 1000 bp fragment is only detected if the nucleic acid in the patient sample is at least 1000 bases long (e.g. 1400 bases or 2500 bases). The presence of a large fragment can be determined, for example, by detecting the entire large fragment or by detecting the presence of smaller fragments (e.g. smaller overlapping fragments) which in combination are indicative or the presence of the large fragment.

Importantly, methods of the invention are independent of the genomic locus detected, and do not require detection of a mutation. Rather, the invention provides for detection of nucleic acid that has avoided apoptotic degradation (although such nucleic acids may have been degraded through other, non-apoptotic mechanisms (e.g. by enzymes). Any *H. pylori* or non-*H. pylori* nucleic acid is useful in the practice of the present invention.

DESCRIPTION OF THE DRAWINGS

FIG. 5A is a gel photograph showing results of amplification of *H. pylori* DNA isolated from stool according to one preferred embodiment of the invention using primers spaced about 200 bp apart. Lanes 1 and 31 are marker lanes, lanes 2 and 15–17 are negative control lanes, and lanes 18–20 are positive control lanes having 50 fg of template, 100 fg of template, or 200 fg of template, respectively. Lanes 3–6 are from one patient diagnosed with an *H. pylori* infection, lanes 7–14 are from a second patient diagnosed with an *H. pylori* infection. For the first patient, lane 3 corresponds to a pre-treatment sample; lane 4 corresponds to day 4 of treatment; lane 5 corresponds to day 10 of treatment; and lane 6 corresponds to day 14 of treatment. For the second patient, lanes 7–9 correspond to pre-treatment samples, lanes 10–13 correspond to days 7, 12, 13, and 18 of treatment, respectively, and lane 14 corresponds to a post-treatment sample.

DETAILED DESCRIPTION OF THE INVENTION

The invention provides methods for the analysis of biological samples. Methods of the invention provide diagnostically-relevant information based upon the presence of high-integrity nucleic acid in a biological sample. The accurate qualitative and/or quantitative determination of the presence of high-integrity nucleic acids in a sample from a patient according to methods of the invention provides information regarding whether a patient has an *H. pylori* infection; whether an infection is worsening or diminishing; whether a course of treatment is successfully treating an infection; and whether a patient who had been diagnosed with an *H. pylori* infection has now been cured. Methods of the invention may also provide an indication of the current degree of severity (grade) of an infection.

Methods of the invention for detecting an *H. pylori* infection comprise detecting an intact nucleic acid in a sample from a patient.

Figure 1:
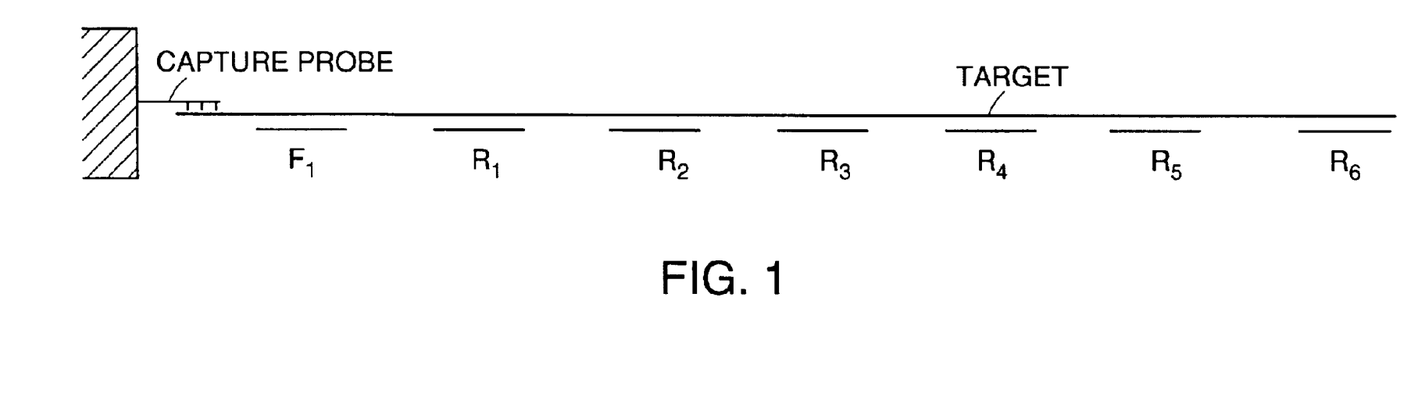
FIG. 1 shows a schematic representation of the placement of primers for amplification in a method of the present invention. In this method, a single forward primer, $F_1$, is used in conjunction with a series of reverse primers, $R_1$ to $R_6$, chosen to amplify progressively longer portions of the target.

In one preferred embodiment, methods of the invention comprise amplifying sequences of different length in a sample, if present, in order to generate a profile of amplification products indicative of an *H. pylori* infection. In a preferred method, a sample is exposed to a set of PCR primers comprising a single forward primer, which may be a capture probe used to capture target fragments, and a plurality of downstream reverse primers which hybridize to portions of a contiguous sequence (if present) in the sample. Amplifications using these primers will result in a series of amplification products, each having a different length, if the contiguous target sequence is present in the sample. The lengths of the amplification products are determined by the spacings between the forward primer and each of the downstream reverse primers. An example is shown in FIG. 1, which is a schematic representation showing placement of primers for amplification.

If the target sequence, or a portion of it, is present in the sample, amplification will result in a series of fragments the length of which is dictated by the spacing of the primers. In a preferred embodiment, the forward primer is designed to hybridize about 200 bp upstream of the first reverse primer, and about 2.3 Kb upstream of the last reverse primer. Other reverse primers are designed to hybridize at various locations between the first and last reverse primers. Preferred intervals between the forward primer and the various reverse primers are 200 bp ($F_1$–$R_1$), 400 bp ($F_1$–$R_2$), 800 bp ($F_1$–$R_3$), 1.3 Kb, ($F_1$–$R_4$), 1.8 Kb ($F_1$–$R_5$), and 2.3 Kb ($F_1$–$R_6$). The number and spacing of reverse primers is chosen at the convenience of the skilled artisan.

Also in a preferred embodiment, a hybrid capture probe is used to anchor a target sequence, preferably on a solid support (e.g., beads). A plurality of probes are then placed at various distances downstream of the capture probe. Those probes can be pairs of forward and reverse primers as discussed above, or they can be signal amplification probes, such as those used in Ligase Chain Reaction (LCR), and others used in the identification of sequences. The plurality of probes hybridize along the length of a target fragment if the target is present in the sample. Thus, by interrogating samples for the presence of the probes, one can determine the integrity of sequences present in the sample. This can be done in numerous ways, including, but not limited to, hybrid capture, PCR, LCR, strand displacement, branched chain, or other assays known in the art that incorporate hybrid probes or primers in order to identify or quantitate sequence. A sample containing high-integrity nucleic acids represents a positive screen according to the invention. In one embodiment, sample is placed into wells (e.g., on a 96 well plate) containing support-bound capture probe. The capture probe immobilizes a target sequence, if present in the sample. Probes that hybridize to sequence downstream of the capture probe (downstream probes) are placed into each well, such that each downstream probe is spaced a unique distance apart from the common capture probe, and each well contains only one type of downstream probe. Signal is then generated by, for example, amplification, or by standard ELISA procedure followed by amplification, or by LCR, or other methods mentioned above. The presence of signal in each well indicates the presence of sequence of at least the length between the capture probe and the downstream probe. In an alternative embodiment, each well receives multiple different downstream probes, which may be distinctly labeled, and the presence of label(s) is correlated with the integrity of a nucleic acid present in the sample.

A sample from a patient having an ongoing *H. pylori* infection produces amplicon between one or more of the primer pairs (depending, inter alia, on the length of the target fragments, on the spacing of the primers, and where on the target the primers are spaced). Such a profile represents a positive screen for infection. A sample from a patent who does not have an infection results in little or no amplification product in the assay described above. Any convenient target nucleic acid locus may be used in the methods of the invention.

The amplification reactions described above may be conducted according to any suitable or convenient protocol and the fragment size of the resulting amplification products (if any) may be determined by any suitable or convenient means.

Figure 2:
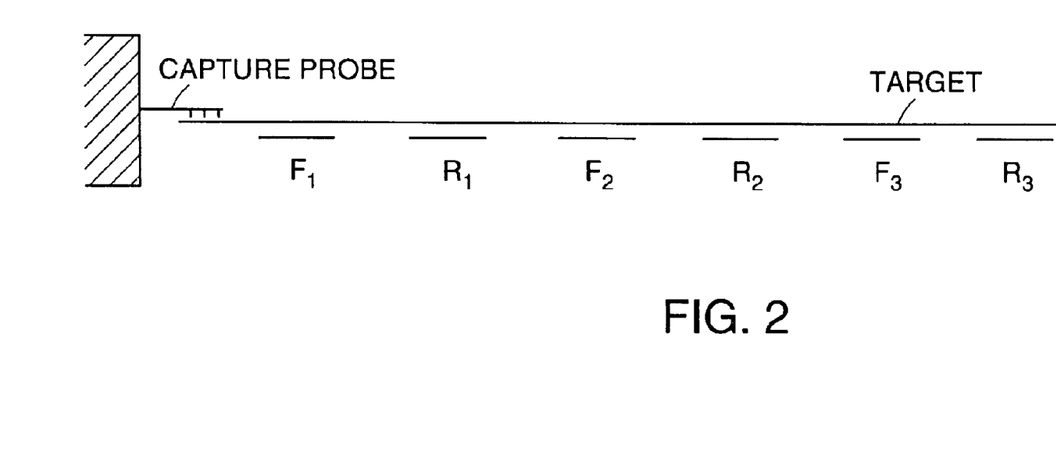
FIG. 2 shows a schematic representation of the placement of the primers for amplification in a method of the present invention. In this method, a series of forward and reverse primer pairs, ($F_1$, $R_1$) to ($F_3$, $R_3$), are chosen to amplify portions of the target spaced at intervals along the target.

In an alternative embodiment, methods of the invention comprise conducting a series of amplification reactions on a contiguous nucleic acid target fragment, each application reaction comprising one forward primer and one reverse primer, such that pairs of forward and reverse primers are spaced at intervals on a contiguous fragment suspected to be in the sample. An example of this arrangement is shown in FIG. 2. Preferably, the spacings between each forward and reverse primer pair are equivalent. In a positive screen, the assay described above will result in a series of same-size fragments for most if not all of the primer pairs. Such an array of amplification products evidences a contiguous target sequence indicative of infection (see above). A sample from a disease-free patient should produce little or no amplification product, but in any case will not produce the contiguous array of amplification products expected from a sample containing a relatively intact diagnostic target sequence.

Each of the methods described above are based upon the principle that an intact nucleic acid, or a segment of an intact nucleic acid, in a sample is diagnostic. Thus, variations on the methods described above are contemplated. Such variations include the placement of primers, the number of primers used, the target sequence, the method for identifying sequences, and others. For example, in the method depicted in FIG. 2, and described above, it is not necessary that the numbers of forward and reverse primers be equal. A forward primer may, for example, be used to amplify fragments between two reverse primers. Other variations in primer pair placement are within the skill in the art, as are details of the amplification reactions to be conducted. Finally, as represented in FIGS. 1 and 2, capture probes may be used in methods of the invention in order to isolate a chosen target sequence.

Because an *H. pylori* infection may be associated with the release of non-apoptotic cells (e.g. living epithelial or blood cells, or cells dying by necrosis or other non-apoptotic means) into a patient sample, the invention also provides methods for detecting an infection by detecting the presence of intact patient DNA (e.g. human DNA) in a patient sample. Cells undergoing apoptosis (e.g. cells shed during renewal of the gastrointestinal tract) efficiently cleave their DNA into small fragments. Accordingly, the presence of intact, large fragments in a patient sample is indicative of cells that have not undergone apoptosis. See, e.g., U.S. Ser. Nos. 09/455, 950 and 09/514,865, the disclosures of which are herein incorporated by reference. Thus, the presence or status of an *H. pylori* infection is determined by detecting either an intact *H. pylori* nucleic acid or an intact patient nucleic acid, or both, according to methods of the invention.

The following examples provide further details of methods according to the invention. For purposes of exemplification, the following examples provide details of the use of the method of the present invention in detecting an *H. pylori* infection. Accordingly, while exemplified in the following manner, the invention is not so limited and the skilled artisan will appreciate its wide range of application upon consideration thereof.

Exemplary Method for the Detection of an *H. pylori* Infection

The following example relates to detecting an *H. pylori* infection using voided stool samples. Based upon the principles upon which the invention is based (see above), the same analysis can be performed on other samples, such as those mentioned above, with the same results as shown herein.

For the analysis of stool samples, preferred methods of the invention comprise obtaining at least a cross-sectional or circumferential portion of a voided stool as taught in U.S. Pat. Nos. 5,741,650 and 5,952,178, both of which are incorporated by reference herein. While a cross-sectional or circumferential portion of stool is desirable, methods provided herein are conducted on random samples obtained from voided stool, which include smears or scrapings. Once obtained, the stool specimen is homogenized. A preferable buffer for homogenization is one that contains at least 16 mM of an ion chelator such as ethylenediaminetetraacetic acid (EDTA). However, as taught in co-owned U.S. patent application Ser. No. 09/491,093, incorporated by reference herein, it has been discovered that the use of at least 150 mM EDTA greatly improves the yield of nucleic acid from stool. Thus, a preferred buffer for stool homogenization comprises phosphate buffered saline, 20–100 mM NaCl or KCl, at least 150 mM EDTA, and optionally a detergent (such as SDS) and a proteinase (e.g., proteinase K).

After homogenization, nucleic acid is preferably isolated from the stool sample. Isolation or extraction of nucleic acid is not required in all methods of the invention, as certain detection techniques can be adequately performed in homogenized stool without isolation of nucleic acids. In a preferred embodiment, however, homogenized stool is spun to create a supernatant containing nucleic acids, proteins, lipids, and other cellular debris. The supernatant is treated with a detergent and proteinase to degrade protein, and the nucleic acid is phenol-chloroform extracted. The extracted nucleic acids are then precipitated with alcohol. Other techniques can be used to isolate nucleic acid from the sample. Such techniques include hybrid capture and amplification directly from the homogenized stool. Nucleic acids can be purified and/or isolated to the extent required by the screening assay to be employed. Total DNA is isolated using techniques known in the art.

Detection Assay Protocol

A preferred detection assay uses PCR to amplify *H. pylori* DNA with specific is primers. Methods for implementing PCR are well-known. The presence of an *H. pylori*-specific amplicon produced by PCR represents a positive screen. Other amplification reactions and modifications of PCR, such as ligase chain reaction, reverse-phase PCR, Q-PCR, and others may be used to produce detectable levels of amplicon. Amplicon may be detected by coupling to a reporter (e.g. fluorescence, radioisotopes, and the like), by sequencing, by gel electrophoresis, by mass spectrometry, or by any other means known in the art, as long as the length, weight, or other characteristic of the amplicons identifies them.

EXAMPLES

Experiments were conducted to determine whether characteristics of amplifiable DNA in stool were indicative of H. pylori infections in patients from whom stool samples were obtained. In the first and second examples, the amount of amplifiable DNA was measured in each of several stool samples using PCR amplification to detect H. pylori DNA fragments in the sample of at least 200 base pairs in length. The third and fourth examples determined profiles of amplification products with nucleic acid fragment lengths of 200 bp, 400 bp, 800 bp, 1.3 Kb, 1.8 Kb and 2.4 Kb.

Example 1

Stool samples were collected from 9 patients previously diagnosed with H. pylori infections and from 9 patients known not to have H. pylori infections. All biopsy samples were examined and graded by pathology and immunohistochemistry. Each stool sample was frozen. Each frozen stool specimen was thawed and homogenized in 500 mM Tris, 150 mM EDTA, and 10 mM NaCl, pH 9.0 at a volume to mass ratio of 7:1. Samples were then rehomogenized in the same buffer to a final volume-to-mass ratio of 20:1, and spun in glass macro beads at 2356×g. The supernatant was collected and treated with SDS, proteinase k and RNAse. The DNA was then precipitated with alcohol. The precipitate was suspended in 10 mM Tris and 1 mM EDTA (1×TE), pH 7.4.

H. pylori DNA was then purified by hybrid capture using a biotinylated H. pylori capture probe (SEQ ID NO:1). A 10 μl aliquot of each probe (20 pmol/capture) was added to a suspension containing 300 μl DNA in the presence of 310 μl 6M GITC buffer for 2 hours at room temperature. Hybrid complexes were isolated using streptavidin-coated beads (Dynal). After washing, probe-bead complexes were suspended at 25° C. for 1 hour in 0.1×TE buffer, pH7.4. The suspension was then heated for 4 minutes at 85° C., and the beads were removed.

Captured DNA was then amplified using PCR, essentially as described in U.S. Pat. No. 4,683,202, incorporated by reference herein. 10 μL of each sample was amplified in a 50 μL reaction for 40 cycles using the primers disclosed in SEQ ID NO:2 and SEQ ID NO:3. Amplified DNA was placed on a 4% Nusieve (FMC Biochemical) gel (3% Nusieve, 1% agarose), and stained with ethidium bromide (0.5 μg/ml). As shown in lanes 2–19 of FIG. 3, an amplified 200 bp H. pylori DNA fragment was detected in every patient known to have an H. pylori infection, but in no patient known to be free of H. pylori infection. Accordingly, the amount of 200 bp H. pylori DNA in a sample was predictive of patient disease status.

Figure 3:
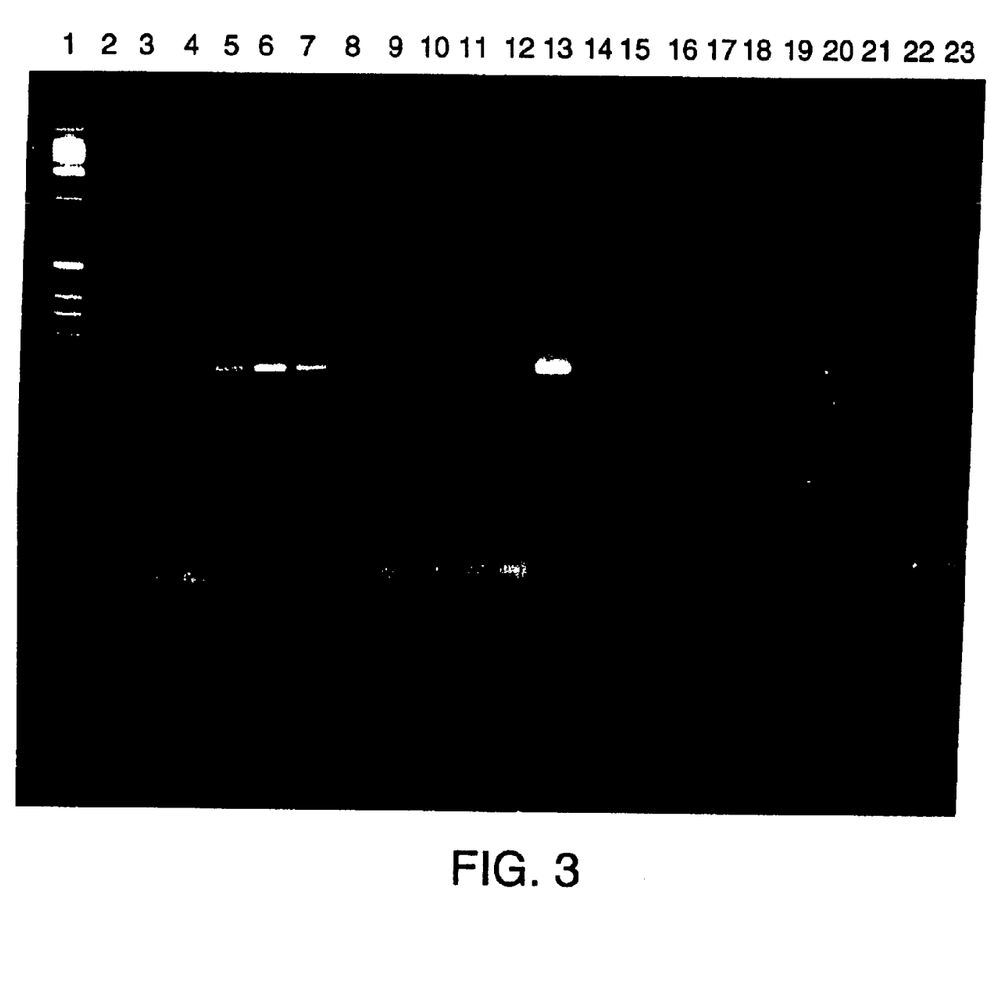
FIG. 3 is a gel photograph showing results of amplification of *H. pylori* DNA isolated from stool according to one preferred embodiment of the invention using forward and reverse primers spaced about 200 bp apart. The band intensity relates to the amount of 200 bp product in the sample. Lane 1 is a marker lane. Lanes 2–4, 8, 10–12, 14 and 15 are from patients without an *H. pylori* infection. Lane 7 is from a patient with a grade 1 *H. pylori* infection. Lanes 5, 6, 9, and 16–19 are from patients with grade 2 *H. pylori* infections. Lane 13 is from a patient with a grade 3 *H. pylori* infection. Lanes 20–23 are from a patient diagnosed with an *H. pylori* infection. Lane 20 corresponds to a sample before treatment. Lane 21 corresponds to day 4 of treatment; lane 22, day 10 of treatment; and lane 23, day 14 of treatment.

Furthermore, the amount of the 200 bp amplicon correlates with the known grade of H. pylori infection. For example, the greatest amount of 200 bp amplicon was detected in sample from the patient with the highest grade of infection (grade 3: FIG. 3, lane 13). Thus, the amount of 200 bp amplicon predicts not only the presence or absence of an infection, but may also predict the degree of severity of the infection.

Example 2

An experiment monitoring a course of treatment for an H. pylori infection was conducted under conditions essentially identical to those described above in Example 1. Stool samples were taken from an individual diagnosed with an H. pylori infection. The first sample was taken before treatment for the infection; subsequent samples were taken on day 4, day 10, and day 14 of the treatment. Patients were treated with a standard triple-therapy treatment regimen for two weeks. Stool samples were treated essentially as described in Example 1.

The results are shown in lanes 20–23 of FIG. 3. As shown in lane 20, a 200 bp H. pylori amplicon was detectable from the pre-therapy sample. A lesser amount of the 200 bp amplicon was detectable on day 4 of the therapy (lane 21). No 200 bp amplicon was detected on days 10 or 14 of the therapy (lanes 22 and 23). Accordingly, the amount of the 200 bp amplicon diminished over the course of the therapy, indicating that the infection was being eradicated.

Example 3

An experiment was conducted to determine the molecular weight profile of H. pylori DNA in stool samples from patients with or without diagnosed H. pylori infections. Stool samples were obtained, and DNA was isolated as described above. A primer corresponding to SEQ ID NO:2 was used as the forward primer for PCR as described above; reverse primers SEQ ID NO:3, SEQ ID NO:4, SEQ ID NO:5, SEQ ID NO:6, SEQ ID NO:7, and SEQ ID NO:8 were spaced to amplify fragments of 200 bp, 400 bp, 800 bp, 1.3 Kb, 1.8 Kb, and 2.4 Kb, respectively. Each of 30 PCR reactions were run for 40 cycles. Amplicon was run on a 3% Seakem gel, and stained with ethidium bromide.

Figure 4:
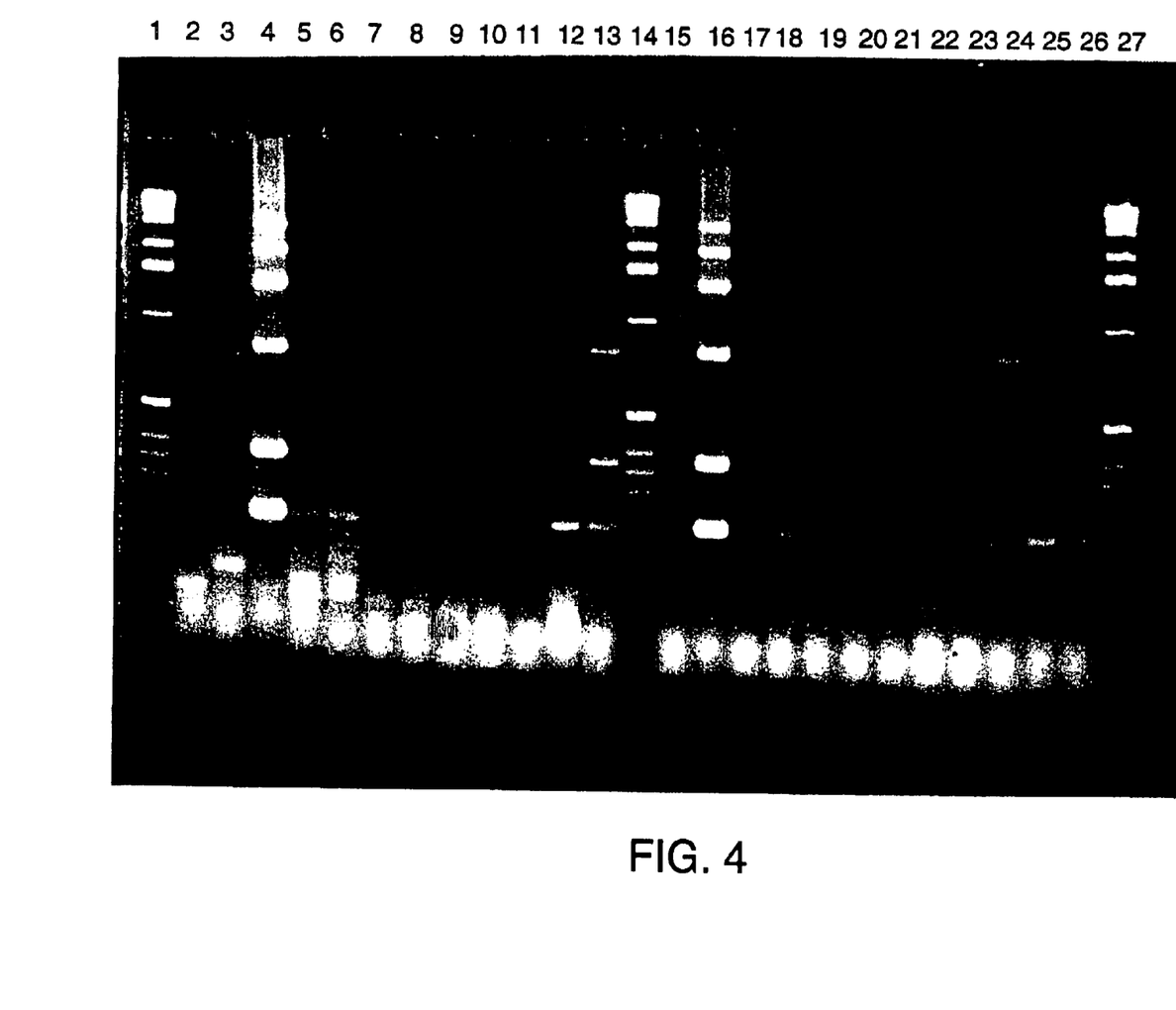
FIG. 4 is a gel photograph showing results of amplification of *H. pylori* DNA isolated from stool according to one preferred embodiment of the invention using a series of primers spaced 200, 400, 800, 1300, 1800, and 2400 bp apart. Lanes 1, 14, and 27 are marker lanes; lanes 2, 15, 22 and 23 are negative control lanes; lanes 11–13 and 24–26 are positive control lanes. Lanes 4 and 16 are from the same patient diagnosed with an *H. pylori* infection; lanes 3 and 17 are from a patient not diagnosed with an *H. pylori* infection. Lanes 5–8 and 18–21 all correspond to samples taken from a single patient. Lanes 5 and 18 are pre-treatment; lanes 6 and 19, day 4 of treatment; lanes 7 and 20, day 10 of treatment; lanes 8 and 21, day 14 of treatment.

As shown in lanes 4 and 16 of FIG. 4, all six fragments were detectable in a patient known to have a severe H. pylori infection. In contrast, none of the fragments were detected in a patient diagnosed as free of H. pylori, as shown in lanes 3 and 17 of FIG. 4. Thus, the presence of a plurality of amplifiable fragments of H. pylori DNA of varying sizes can be used do determine disease status, and even high molecular weight species of intact H. pylori DNA are detectable in a patient having a high grade infection.

Example 4

Stool samples from the patient of Example 2 were analyzed as described in Example 3 to determine the molecular weight profile of H. pylori DNA in stool samples over the course of treatment of the infection. The results are shown in lanes 5–8 and 18–21 of FIG. 4. As shown in lanes 5 and 18, the 200 bp amplicon was reproducibly detectable in the pre-therapy sample; in lane 18 the 400 bp amplicon was also detected. In the sample from therapy day 4, the 200 bp amplicon was still reproducibly detectable, as shown in lanes 6 and 19; in lane 19, the 400 bp amplicon was also detected. No amplified H. pylori DNA was detected in the day 10 or day 14 samples.

Example 5

Stool samples from the patient of Example 2 and from a second patient diagnosed with an H. pylori infection were taken before and during treatment for the infection; one further sample from the second patient was taken after treatment was complete. Samples were frozen, thawed, and treated as described in Example 1. 300 μL of each sample was subjected to hybrid capture using biotinylated oligonucleotides complementary to H. pylori (SEQ ID NO:1) and human APC (SEQ ID NO:9) gene specific sequences. Hybrid captured sequences were eluted with 35 μL TE and independent PCR reactions were performed for the *H. pylori* (as described in Example 1) and human APC target sequences (using oligonucleotides corresponding to SEQ ID NO:10 and SEQ ID NO:11). The PCR products were resolved on a 4% agarose gel and stained with ethidium bromide.

Figure 5A:
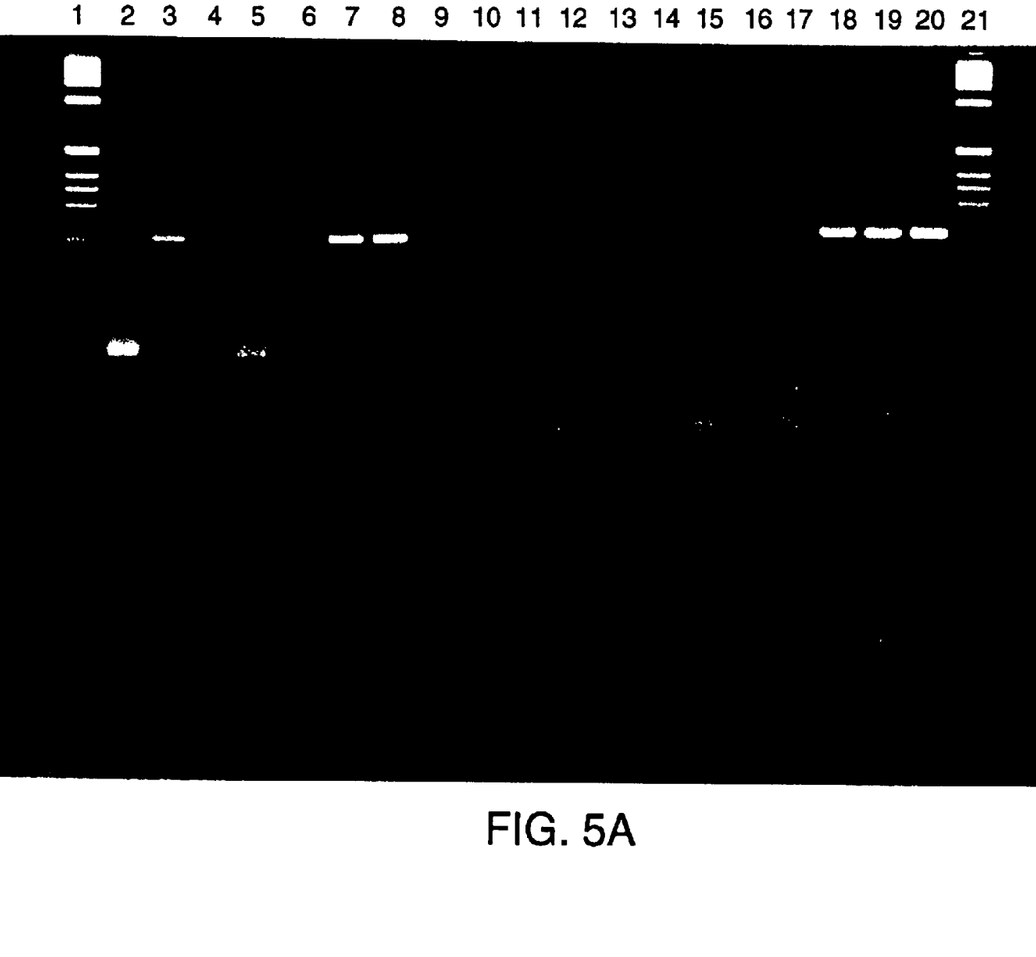
Figure 5B:
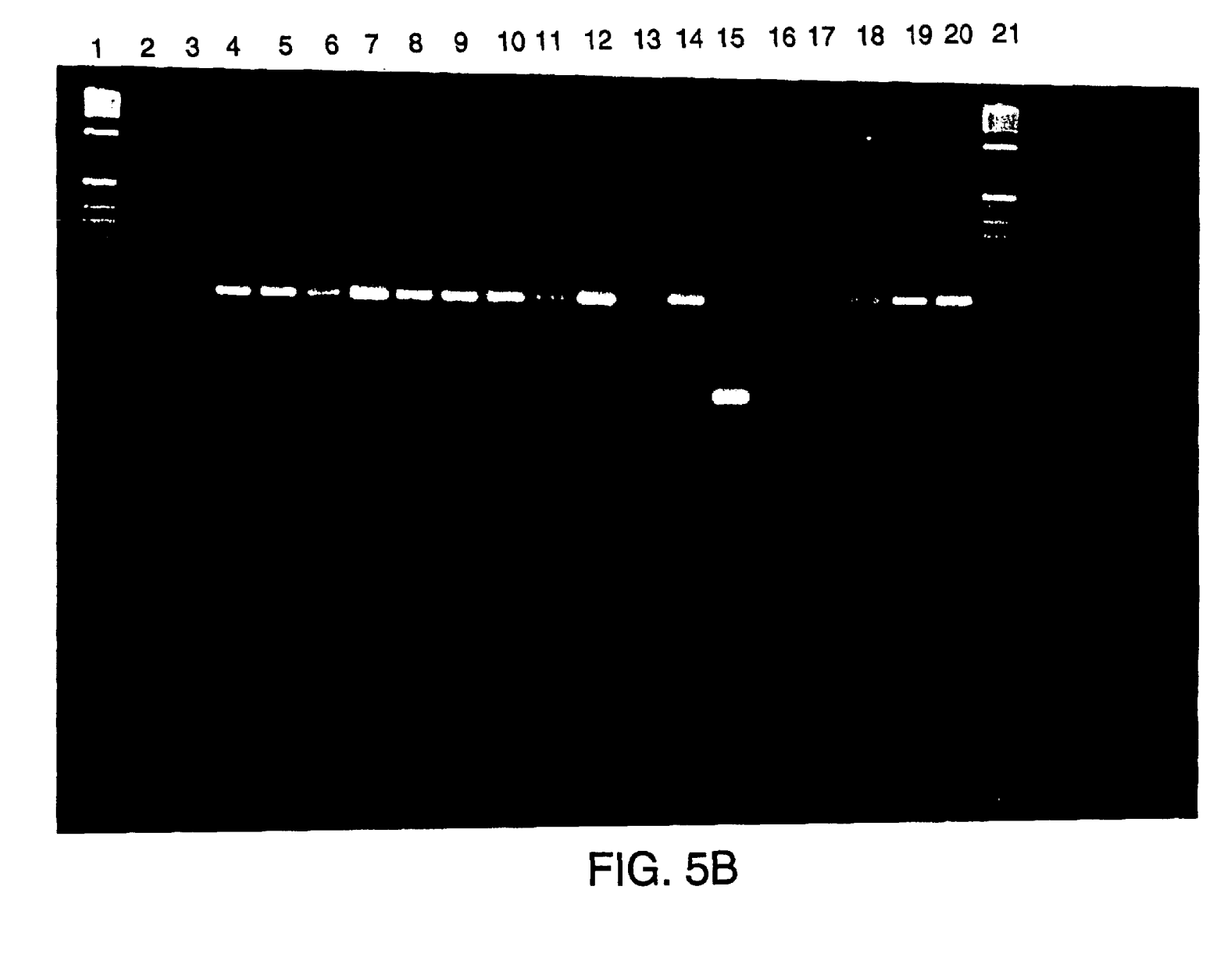
FIG. 5B is a gel photograph showing results of amplification of a human DNA isolated from stool according to one preferred embodiment of the invention using primers spaced about 200 bp apart. Positive control lanes, negative control lanes, and patient sample lanes are otherwise the same as in FIG. 5A.

As shown in FIG. 5A, *H. pylori* nucleic acid was detected in the pre-treatment sample of the first patient (lane 3) and in all three pre-treatment samples of the second patient (lanes 7–9). After treatment began, less *H. pylori* nucleic acid was detectable (see treatment day 4 of the first patient (lane 4) and treatment day 7 of the second patient (lane 10)) until *H. pylori* nucleic acid was no longer detectable (see treatment days 10 and 14 of the first patient (lanes 5 and 6) and days 12, 13 and 18 and the post-treatment sample from the second patient (lanes 11–14)). In contrast, as shown in the corresponding lanes of FIG. 5B, human nucleic acid was detected in each of the samples.

What is claimed is:

1. A method for detecting a current *Helicobacter pylori* infection, the method comprising the steps of:

detecting a *Helicobacter pylori* nucleic acid present in a patient stool sample; and     identifying the patient as having a current *Helicobacter pylori* infection if the nucleic acid is present in a length of at least 175 base pairs and in an amount indicative of infection, the amount exceeding an amount indicative of an absence of current *Helicobacter pylori* infection.

2. A method for detecting a current *Helicobacter pylori* infection, the method comprising the steps of:

detecting a high-integrity *Helicobacter pylori* nucleic acid having a length of at least 175 base pairs present in a patient stool sample;

comparing an amount of high-integrity *Helicobacter pylori* nucleic acid present in the patient sample to an amount of a non-*Helicobacter pylori* nucleic acid present in the patient sample; and identifying the patient as having a current *Helicobacter pylori* infection if the relative amount of high-integrity *Helicobacter pylori* nucleic acid and of non-*Helicobacter pylori* nucleic acid exceeds a reference amount.

3. The method of claim 2, wherein the non-*Helicobacter pylori* nucleic acid is a human nucleic acid.

4. The method of claim 2, wherein the non-*Helicobacter pylori* nucleic acid is an *Escherichia coli* nucleic acid.

5. The method of claim 2, wherein the patient sample is selected from the group consisting of stool, sputum, pancreatic fluid, bile, lymph, blood, urine, saliva, gastric juice, and vomitus.

6. The method of claim 5, wherein the patient sample is stool.

7. The method of claim 5, wherein the patient sample is saliva.

8. The method of claim 1, wherein the *Helicobacter pylori* nucleic acid is a DNA.

9. The method of claim 1, comprising the further step of adding an ion chelator to the patient sample such that the concentration of the ion chelator is at least 150 mM.

10. A method for detecting a *Helicobacter pylori* infection in a patient, the method comprising the steps of:

amplifying, from a patient sample,
      a first *Helicobacter pylori* nucleic acid at least 200 nucleotides in length,
      a second *Helicobacter pylori* nucleic acid at least 400 nucleotides in length, and
      a third *Helicobacter pylori* nucleic acid at least 600 nucleotides in length;

detecting the amplified first, second, and third *Helicobacter pylori* nucleic acids; and identifying the patient as having a *Helicobacter pylori* infection if the amplified first, second, and third *Helicobacter pylori* nucleic acids are detected.

11. A method for detecting a *Helicobacter pylori* infection in a patient, the method comprising the steps of:

detecting a human nucleic acid in a patient stool sample comprising shed cells or cellular debris; and identifying the patient as having disease if the length of the nucleic acid is indicative of infection, wherein the length of the nucleic acid is indicative of infection if the nucleic acid comprises at least 175 base pairs.

12. The method of claim 11, wherein the human nucleic acid has a length of at least 200 nucleotides.

13. The method of claim 1, wherein the amount indicative of infection is a detection threshold.

14. The method of claim 1, further comprising the step of exposing the patient stool sample to an immobilized probe that hybridizes to *Helicobacter pylori* nucleic acid nucleic acids, thereby to immobilize a *Helicobacter pylori* nucleic acid, if present in the patient sample.

* * * * *

```
                         SEQUENCE LISTING

<160> NUMBER OF SEQ ID NOS:   11

<210> SEQ ID NO 1
  <211> LENGTH: 17
  <212> TYPE: DNA
  <213> ORGANISM: Artificial sequence
  <220> FEATURE:
  <223> OTHER INFORMATION: H. pylori capture probe

<400> SEQUENCE: 1
taaaactcaa aggaata                                                  17

<210> SEQ ID NO 2
  <211> LENGTH: 21
  <212> TYPE: DNA
  <213> ORGANISM: Artificial sequence
  <220> FEATURE:
  <223> OTHER INFORMATION: H. pylori forward primer

<400> SEQUENCE: 2
cgttagctgc attactggag a                                             21

<210> SEQ ID NO 3
  <211> LENGTH: 20
  <212> TYPE: DNA
  <213> ORGANISM: Artificial sequence
  <220> FEATURE:
  <223> OTHER INFORMATION: H. pylori reverse primer 1

<400> SEQUENCE: 3 tagggtaaa atccgtagag                                                20

<210> SEQ ID NO 4
  <211> LENGTH: 19
  <212> TYPE: DNA
  <213> ORGANISM: Artificial sequence
  <220> FEATURE:
  <223> OTHER INFORMATION: H. pylori reverse primer 2

<400> SEQUENCE: 4
caagcgttac tcggaatca                                                19

<210> SEQ ID NO 5
  <211> LENGTH: 19
  <212> TYPE: DNA
  <213> ORGANISM: Artificial sequence
  <220> FEATURE:
  <223> OTHER INFORMATION: H. pylori reverse primer 3

<400> SEQUENCE: 5
cgggtgagta acgcatagg                                                19
```

-continued

```
<210> SEQ ID NO 6
<211> LENGTH: 20
<212> TYPE: DNA
<213> ORGANISM: Artificial sequence
<220> FEATURE:
<223> OTHER INFORMATION: H. pylori reverse primer 4

<400> SEQUENCE: 6
tcatttcctt gtttcagcaa                                              20

<210> SEQ ID NO 7
<211> LENGTH: 20
<212> TYPE: DNA
<213> ORGANISM: Artificial sequence
<220> FEATURE:
<223> OTHER INFORMATION: H. pylori reverse primer 5

<400> SEQUENCE: 7
cgccgatttt agagacgatt                                              20

<210> SEQ ID NO 8
<211> LENGTH: 18
<212> TYPE: DNA
<213> ORGANISM: Artificial sequence
<220> FEATURE:
<223> OTHER INFORMATION: H. pylori reverse primer 6

<400> SEQUENCE: 8
ggcgatcaca cgatggaa                                                18

<210> SEQ ID NO 9
<211> LENGTH: 37
<212> TYPE: DNA
<213> ORGANISM: Artificial sequence
<220> FEATURE:
<223> OTHER INFORMATION: APC capture probe

<400> SEQUENCE: 9
cagatagccc tggacaaacc atgccaccaa gcagaag                           37

<210> SEQ ID NO 10
<211> LENGTH: 20
<212> TYPE: DNA
<213> ORGANISM: Artificial sequence
<220> FEATURE:
<223> OTHER INFORMATION: APC forward primer

<400> SEQUENCE: 10
cacctccacc acctcctcaa                                              20

<210> SEQ ID NO 11
<211> LENGTH: 19
<212> TYPE: DNA
<213> ORGANISM: Artificial sequence
<220> FEATURE:
<223> OTHER INFORMATION: APC reverse primer

<400> SEQUENCE: 11
gtatcagcat ctggaagaa                                               19
```